(12) United States Patent
Bikko

(10) Patent No.: US 9,788,757 B2
(45) Date of Patent: Oct. 17, 2017

(54) BREATHING BIOFEEDBACK DEVICE

(75) Inventor: Nirinjan Bikko, Walnut Creek, CA (US)

(73) Assignee: BREATH RESEARCH, INC., Walnut Creek, CA (US)

(*) Notice: Subject to any disclaimer, the term of this patent is extended or adjusted under 35 U.S.C. 154(b) by 2501 days.

(21) Appl. No.: 11/645,207

(22) Filed: Dec. 21, 2006

(65) Prior Publication Data

US 2007/0173730 A1    Jul. 26, 2007

Related U.S. Application Data

(60) Provisional application No. 60/754,824, filed on Dec. 28, 2005.

(51) Int. Cl.
| | | |
|---|---|---|
| A61B 5/08 | (2006.01) | |
| A61B 7/00 | (2006.01) | |
| A61B 5/00 | (2006.01) | |
| A61M 21/00 | (2006.01) | |

(52) U.S. Cl.
CPC .......... *A61B 5/0803* (2013.01); *A61B 5/486* (2013.01); *A61B 5/6803* (2013.01); *A61B 7/003* (2013.01); *A61B 5/08* (2013.01); *A61B 5/7264* (2013.01); *A61B 5/7405* (2013.01); *A61H 2201/5048* (2013.01); *A61M 2021/0027* (2013.01)

(58) Field of Classification Search
CPC .......... A61B 5/486; A61B 7/003; A61B 5/08; A61B 5/7264; A61B 5/0816; A61B 5/7405; A61B 5/4806; A61M 2021/0027; A61H 2201/5048
USPC ................................................. 600/529–543
See application file for complete search history.

(56) References Cited

U.S. PATENT DOCUMENTS

| | | | | |
|---|---|---|---|---|
| 3,991,304 | A | * | 11/1976 | Hillsman ................ 600/538 |
| 4,063,550 | A | | 12/1977 | Tiep |
| 4,064,869 | A | | 12/1977 | Defares et al. |

(Continued)

FOREIGN PATENT DOCUMENTS

| | | |
|---|---|---|
| EP | 0 145 160 A2 | 6/1985 |
| EP | 0804938 | 11/1997 |

(Continued)

OTHER PUBLICATIONS

Extended European Search Report mailed Aug. 8, 2011 in EP Application No. 06 84 9045, 7 pages.

*Primary Examiner* — Patricia Mallari
*Assistant Examiner* — Karen Toth

(57) ABSTRACT

A breathing biofeedback device, having a microphone configured to acquire sounds of a user's breathing; a controller communicatively connected with the microphone, the controller processing the signals acquired by the microphone to produce an output signal, the controller processing the signal whereby the microphone signal is first pre-amplified to a voltage level that can be processed by an audio envelope detector circuit, the envelope detector signal is then fed into the analog-to-digital converter input of the controller allowing it to constantly sample the input volume level, the controller then controlling the output volume level fed to the headphones utilizing a digitally controlled variable-gain amplifier, wherein the output signal is not modified in any manner from the original input, except in volume; and a pair of earphones connected with the controller and configured to convey the output signal to the user.

8 Claims, 4 Drawing Sheets

(56) References Cited

U.S. PATENT DOCUMENTS

| | | | |
|---|---|---|---|
| 4,143,648 A * | 3/1979 | Cohen et al. | 600/23 |
| 4,215,431 A * | 7/1980 | Nady | 455/43 |
| 4,220,142 A | 9/1980 | Rosen et al. | |
| 4,337,445 A * | 6/1982 | Akagiri | 333/14 |
| 4,644,330 A * | 2/1987 | Dowling | 340/575 |
| 4,798,538 A | 1/1989 | Yagi | |
| 4,848,360 A * | 7/1989 | Palsgard et al. | 600/586 |
| 4,924,876 A * | 5/1990 | Cameron | 600/538 |
| 4,981,295 A | 1/1991 | Belman et al. | |
| 5,076,281 A | 12/1991 | Gavish | |
| 5,137,501 A | 8/1992 | Mertesdorf | |
| 5,444,786 A | 8/1995 | Raviv | |
| 5,477,867 A * | 12/1995 | Balkanyi | 128/848 |
| 5,633,473 A * | 5/1997 | Mori | G10H 3/146 84/625 |
| 5,779,484 A | 7/1998 | Lampotang et al. | |
| 5,800,337 A | 9/1998 | Gavish | |
| 5,810,722 A | 9/1998 | Heikkila | |
| 5,879,313 A | 3/1999 | Raviv et al. | |
| 5,899,203 A * | 5/1999 | Defares et al. | 128/204.23 |
| 5,936,464 A * | 8/1999 | Grondahl | H03F 1/0222 330/10 |
| 6,027,463 A * | 2/2000 | Moriyasu | 601/46 |
| 6,056,703 A | 5/2000 | Sandler et al. | |
| 6,064,964 A | 5/2000 | Yamamoto et al. | |
| 6,090,037 A | 7/2000 | Gavish | |
| 6,134,331 A * | 10/2000 | Bækgaard | 381/67 |
| 6,142,950 A | 11/2000 | Allen et al. | |
| 6,261,238 B1 * | 7/2001 | Gavriely | 600/532 |
| 6,273,728 B1 | 8/2001 | Van Meurs et al. | |
| 6,411,850 B1 | 6/2002 | Kay et al. | |
| 6,423,013 B1 * | 7/2002 | Bakker et al. | 600/586 |
| 6,626,843 B2 | 9/2003 | Hillsman | |
| 6,662,032 B1 * | 12/2003 | Gavish et al. | 600/323 |
| 6,889,033 B2 * | 5/2005 | Bongfeldt | 455/11.1 |
| 6,935,335 B1 | 8/2005 | Lehrman et al. | |
| 7,006,650 B1 | 2/2006 | Wild | |
| 7,390,304 B2 | 6/2008 | Chen et al. | |
| 7,554,028 B2 * | 6/2009 | Fujii | 84/741 |
| 7,559,903 B2 | 7/2009 | Moussavi et al. | |
| 7,785,249 B2 * | 8/2010 | Schachter et al. | 600/27 |
| 8,092,381 B2 | 1/2012 | Edwards | |
| 8,768,489 B2 | 7/2014 | Thieberger et al. | |
| 8,834,364 B2 | 9/2014 | Heneghan et al. | |
| 2002/0090921 A1 * | 7/2002 | Midtgaard | H03F 1/3247 455/126 |
| 2003/0072457 A1 | 4/2003 | Grasfield et al. | |
| 2003/0130595 A1 | 7/2003 | Mault | |
| 2003/0212338 A1 | 11/2003 | Linck et al. | |
| 2004/0186390 A1 | 9/2004 | Ross et al. | |
| 2004/0225226 A1 | 11/2004 | Lehrman et al. | |
| 2004/0260191 A1 | 12/2004 | Stubbs et al. | |
| 2005/0032496 A1 * | 2/2005 | Saeki | H03G 3/3036 455/234.1 |
| 2005/0068211 A1 * | 3/2005 | Arai | H03M 1/188 341/138 |
| 2005/0124906 A1 | 6/2005 | Childre et al. | |
| 2005/0192508 A1 | 9/2005 | Lange et al. | |
| 2006/0009971 A1 | 1/2006 | Kushner et al. | |
| 2006/0063981 A1 | 3/2006 | Sotos et al. | |
| 2006/0107824 A1 | 5/2006 | Bando et al. | |
| 2006/0198533 A1 | 9/2006 | Wang et al. | |
| 2007/0117075 A1 | 5/2007 | Gordon et al. | |
| 2007/0167855 A1 * | 7/2007 | Shin et al. | 600/533 |
| 2007/0239225 A1 | 10/2007 | Saringer | |
| 2007/0282174 A1 | 12/2007 | Sabatino | |
| 2007/0282212 A1 | 12/2007 | Sierra | |
| 2008/0071137 A1 | 3/2008 | Schachter et al. | |
| 2008/0082017 A1 | 4/2008 | Savic | |
| 2008/0109965 A1 | 5/2008 | Mossbeck | |
| 2009/0118631 A1 | 5/2009 | Gavish et al. | |
| 2009/0312660 A1 | 12/2009 | Guarino et al. | |
| 2010/0069774 A1 * | 3/2010 | Bingham et al. | 600/538 |
| 2010/0174200 A1 * | 7/2010 | Wood et al. | 600/484 |
| 2010/0240945 A1 | 9/2010 | Bikko | |
| 2010/0262031 A1 | 10/2010 | Fu et al. | |
| 2011/0125045 A1 | 5/2011 | Scholz et al. | |
| 2011/0230778 A1 | 9/2011 | Lai et al. | |
| 2011/0295138 A1 | 12/2011 | Lai et al. | |
| 2011/0295139 A1 | 12/2011 | Yang et al. | |
| 2012/0065978 A1 | 3/2012 | Villavicencio | |
| 2012/0071777 A1 | 3/2012 | MacAuslan | |
| 2014/0155773 A1 | 6/2014 | Stamatopoulos et al. | |
| 2014/0350361 A1 | 11/2014 | De Chazal et al. | |

FOREIGN PATENT DOCUMENTS

| | | |
|---|---|---|
| EP | 2925217 | 10/2015 |
| JP | 52-41993 S | 3/1977 |
| WO | 98/14116 A2 | 4/1998 |
| WO | WO2001023040 | 4/2001 |
| WO | 2005/089856 A1 | 9/2005 |
| WO | WO2011132118 | 10/2011 |
| WO | WO2014083079 | 6/2014 |

* cited by examiner

BREATHING BIOFEEDBACK DEVICE

CROSS-REFERENCE TO RELATED APPLICATION

This application claims the benefit of U.S. Provisional Application No. 60/754,824, filed Dec. 28, 2005, the disclosure of which is incorporated herein by reference in its entirety.

BACKGROUND OF THE INVENTION

The present invention relates to an electronic breathing biofeedback device. In particular, the present invention is directed towards a self-contained, wearable biofeedback device, for the purpose of learning to modify and control breathing sound levels and patterns while awake or asleep.

The recording of breathing sounds in general may be known. For example, U.S. Pat. No. 6,261,238 uses multiple sensors to analyze breath sounds. The focus of this patent appears to be on the initial screening, detection, defining, and verification process. However, this device does not feed back the sound of the breath to the patient/client for the purpose of education, modification, and training.

U.S. Pat. No. 4,924,876 is a nasal breath monitor that feeds the sound of the breath back to the patient/client. However, this device only detects breathing sounds from the nose. This patent does not provide for an analysis of the signal volume to provide a feedback.

U.S. Pat. No. 5,477,867 is a device for the suppression of snoring. This device's feedback uses a series of tones which become more and more unpleasant. The use of a tone can be unpleasant and does not increase awareness as a means of making a change in a breathing pattern.

There is therefore a need for a breathing biofeedback device that does not suffer from the above and other shortcomings.

BRIEF SUMMARY OF THE INVENTION

The present invention is directed toward a breathing biofeedback device, having a microphone configured to acquire sounds of a user's breathing; a controller communicatively connected with the microphone, the controller processing the signals acquired by the microphone to produce an output signal, the controller processing the signal whereby the microphone signal is first pre-amplified to a voltage level that can be processed by an audio envelope detector circuit, the envelope detector signal is then fed into the analog-to-digital converter input of the controller allowing it to constantly sample the input volume level, the controller then controlling the output volume level fed to the headphones utilizing a digitally controlled variable-gain amplifier, wherein the output signal is not modified in any manner from the original input, except in volume; and a pair of earphones connected with the controller and configured to convey the output signal to the user while preventing sound leakage that could cause undesirable acoustic feedback. The earphones are preferably configured to stay physically in place while the user is sitting, lying, in motion and sleeping.

For a further understanding of the nature and advantages of the invention, reference should be made to the following description taken in conjunction with the accompanying drawings.

DETAILED DESCRIPTION OF THE INVENTION

The present invention is directed towards a self-contained, wearable biofeedback device, for the purpose of learning to modify and control breathing sound levels and patterns while awake or asleep.

Figure 1:
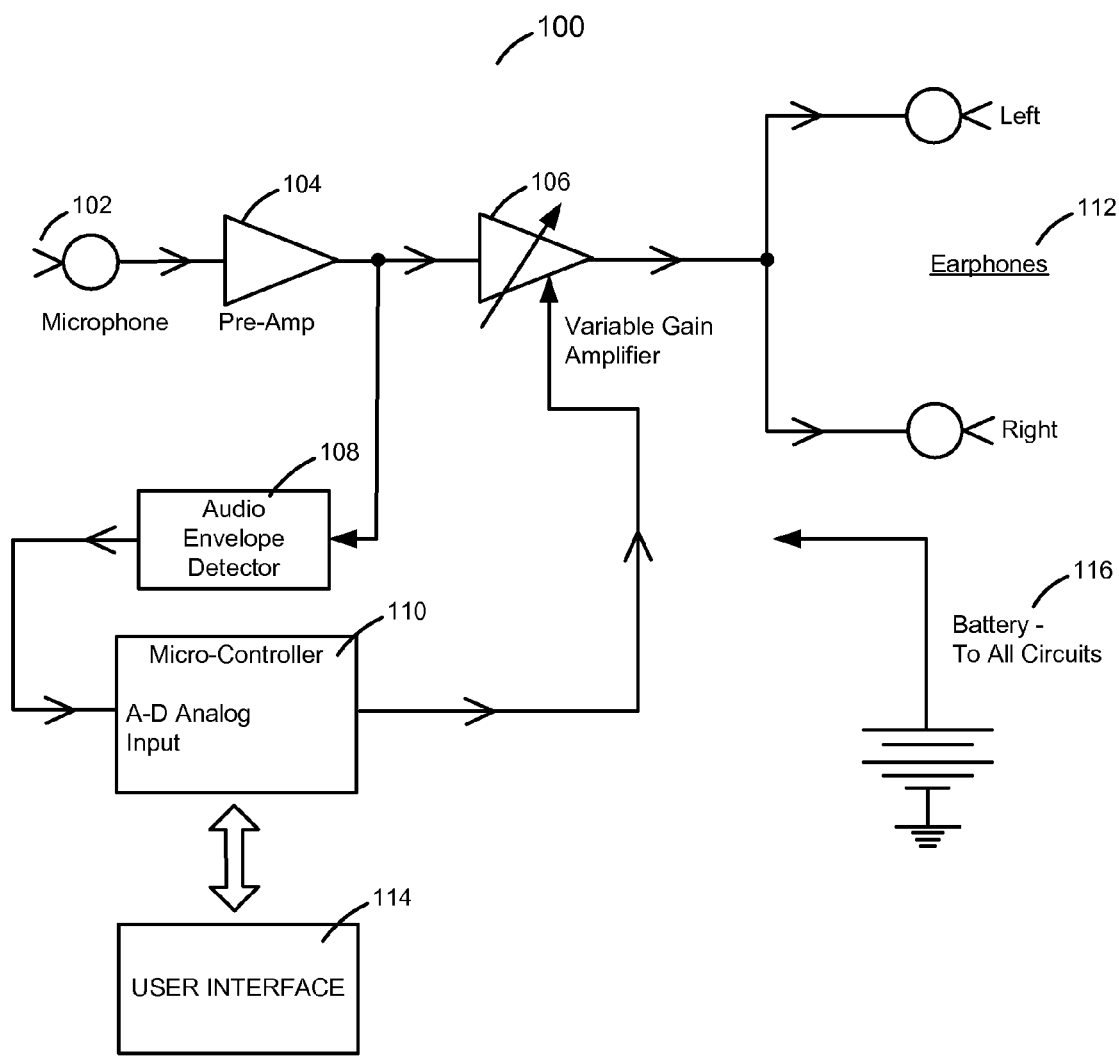
FIG. 1 is an exemplary circuit diagram of one embodiment of the breathing biofeedback device in accordance with the present invention.

FIG. 1 shows an exemplary circuit diagram 100 of one embodiment of the breathing biofeedback device in accordance with the present invention. As is shown in FIG. 1, the device includes a microphone 102 that is used as an input device for receiving a user's breath sounds. The microphone 102 is connected via the preamp 104 to a variable gain amplifier 106. One output of the preamp is fed to an audio envelope detector 108. The output of the audio envelope detector 108 is fed to a controller that can set the gain for the variable gain amplifier 106. The output of the variable gain amplifier 106 is fed to the speakers or earphones 112. The device also includes a user interface 114 having a display configured to interact with the user. The device also includes an appropriate power supply 116.

In one implementation, the breathing biofeedback device can be a small battery-powered device that is partly worn on the user's head (using a headband) in a comfortable manner. There can be a connector from the headband to a display unit where settings can be made and viewed. There can also be a remote control to modify settings. As described above, the breathing biofeedback device can include various subcomponents. These include an input device, an output device, a display unit, a controller or processor, and a user interface that is displayed on the display unit and with which the user or wearer interacts. In addition, the device can include a memory device that can be used to aid the operation of the processor and also to store and delete various received or processed signals or information.

Figure 2:
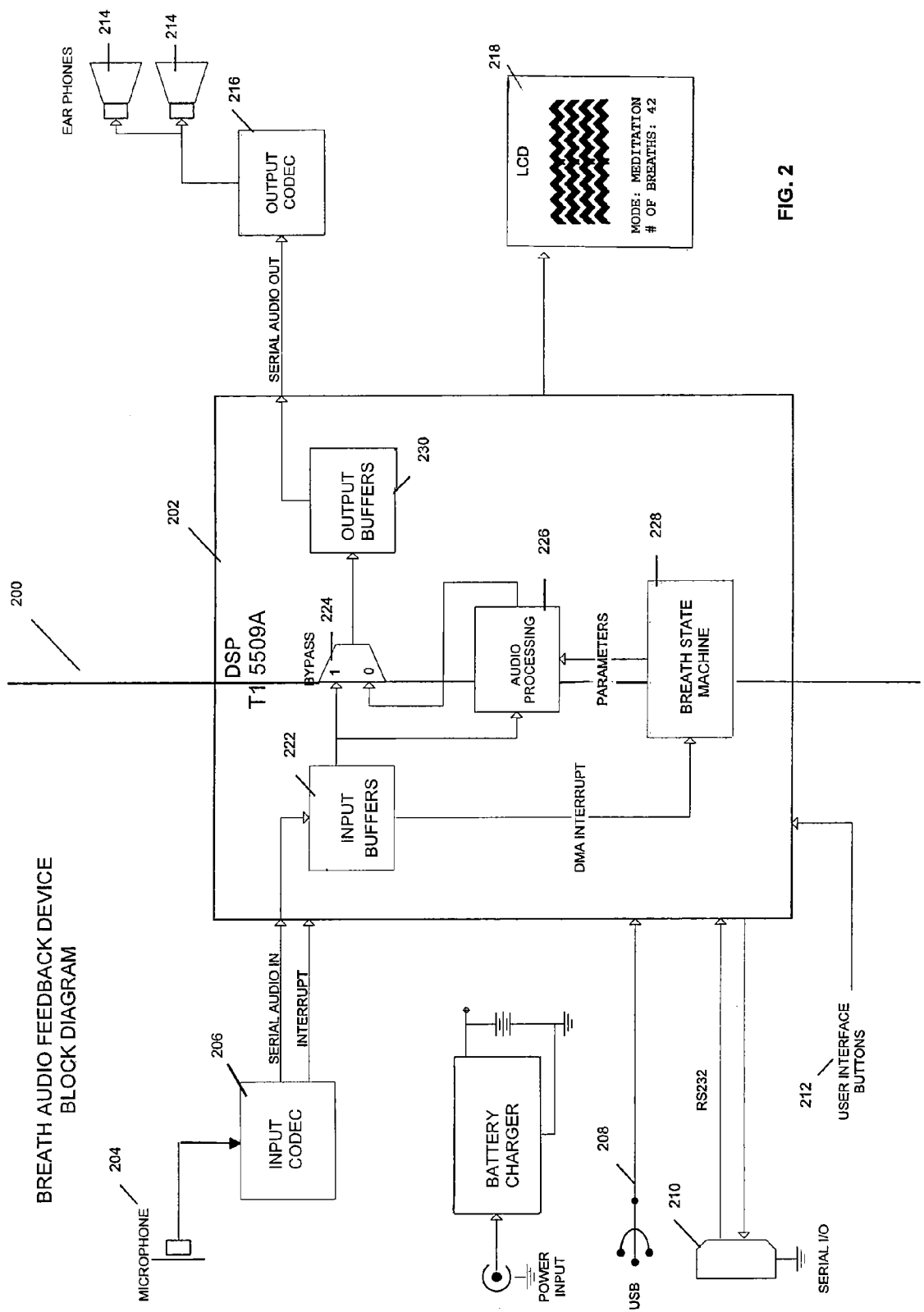
FIG. 2 is an exemplary block diagram of another embodiment of the breathing biofeedback device in accordance with the present invention.

FIG. 2 shows an exemplary block diagram 200 of another embodiment of the breathing biofeedback device in accordance with the present invention. The embodiment of the device shown in FIG. 2, includes a Digital Signal Processor (DSP) 202 that performs the control functions for the device. A microphone 204 is operatively connected with the controller 202 via an input CODEC 206. The input CODEC 206 provides audio input and interrupt signal to the controller 202. The processor 202 can also exchange I/O via a USB 208 and/or a RS232 serial port 210. The controller 202 can also include user interface buttons 212. The controller 202 receives the various input signals, processes them and provides output audio signals to the ear phones via the output CODEC 216. The controller 202 also provides various output signals for display on the display unit 218, which in one embodiment can be an LCD display.

The controller 202 can be a TI 5509A DSP. The controller 202 has an input buffer 222. Input buffer 222 receives input from the audio in and communicates with bypass 224, audio processing 226 and the breath state machine 228. Output from the breath state machine 228, audio processing 226 and the bypass 224 are fed to the output buffers, the earphones 214 and the display device 218.

As described above, the device can be a self-contained, wearable device that provides real-time, interactive, audio biofeedback of the breath. One purpose of this device is to regulate and modify breath patterns, and to support the learning and execution of breathing exercises. It is known that breath patterns contribute significantly to health and illness. Breath awareness and breathing exercises are used in the medical field, the psychological field, and for general health and well being. Breathing exercises are very beneficial, but they can be difficult to learn and execute correctly. The device in accordance with the embodiments of the present invention makes the breath audible to the user in real time. By hearing the breath, neurological connections are made that support breath regulation. Hearing the breath provides more sensory input which makes breathing exercises easier to learn and execute.

In one embodiment, the device in accordance with the embodiments of the present invention can use digital signal audio processing and a Breath State Machine to detect each breath and make the necessary adjustments to provide clean and consistent audio feedback. In addition, the present device can also include specialized modes for different applications, and an effects processor to enhance the sound quality of the breath. Further details of the device and its sub parts are described below.

In one aspect, the device can be a small battery-powered, rechargeable, or plug-in device with a microphone and stereo ear phones (or headphones) that fit on the user's head in a comfortable manner. The device has onscreen display capability. It can stand on its own or be incorporated into mobile and personal devices, computers, biofeedback, medical and exercise equipment.

Input device: The input device can include a single acoustic microphone. The microphone acquires sounds of the users breathing. This microphone can be physically mounted in such a way as to maximize sensitivity to the sounds of breathing (through the mouth and nose) while rejecting unwanted ambient sounds (e.g. to maximize signal to noise ratio). The microphone can be wireless or attached at the other end to a headband. The device uses a microphone sensitive enough to pick up breathing sounds. This can be a surface stethoscope microphone, a condenser microphone, or any other state-of-the-art microphone. The microphone can be positioned in such a way as to maximize sensitivity to breathing sounds while rejecting unwanted ambient sounds. (e.g., maximize signal to noise ratio). The input device can be placed near the mouth, nose, throat, thorax, head or other part.

Output device: The output device can include binaural earphones. The earphones are configured to convey the output signal to the user while preventing sound leakage that could cause undesirable acoustic feedback. The earphones are configured to be comfortable and stay physically in place while the user is sitting, lying, in motion and sleeping. Other head pieces can be available for particular applications.

Display unit: The display unit can be a PDA, laptop, or a PC or an equivalent intelligent host device. A software program provides an interface with the headband unit. The display unit can also include a separate speaker(s). In one embodiment, the display unit includes a VGA LCD screen with a DXVU meter or other equivalent meter. The display can show basic setup information, status and menus. The DXVU meter can provide a visual display of frequency response. The DXVU meter is an ActiveX control, which can monitor any audio device configured as a recording source, such a Microphone, CD ROM, etc. and display the monitored audio levels like a standard VU Meter or as an oscilloscope.

For power, options can include dry-cell batteries and lithium-ion rechargeable batteries. All units include an AC adaptor power supply.

A remote control unit: A remote control unit can be used with the device so the user can manually adjust volume, settings, timer, and so on.

The user interface: The user interface is configured to receive input and provide operational information to the user. The user interface provides various parameters and functionality, including: an ability to interact with the display (e.g. an LCD display) and pushbuttons, etc. The user interface and the device include features for: an on/off switch; volume level control; mode select buttons and indicators. The mode and their available selections include: snoring/sleep apnea with settings for volume output level—baseline, threshold volume, time interval for response to feedback, pitch—volume ratio/limits, statistical analysis (see below); breath training with settings for volume output level, pitch +/−, special effects, reverb (i.e. stadium preset), frequency manipulation; and a timer having a pleasant alarm.

In one aspect, the user interface of the device offers the user the following controls, namely: an on/off switch; a volume control dial; various menu buttons, and navigation controls. The menu on the user interface can be configured to give the user access to setup options, mode selection and features. The setup functions can include: microphone type; earphone type; breath calibration time and personalized setting option. Mode selection functions can include: basic; stress reduction/relaxation; anti-snoring; and fitness training/cardio. Feature settings can include: effects processor and timer.

The output display of the device as a user interface display provides the user with information gathered by the device while operating in one of its several states. In one embodiment, the states include: breath calibration, duration of breath cycle, volume/frequency averages and peaks, and output volume. This data can be saved to the device's memory; the user can delete the information as needed.

As set forth above, the device in accordance with the embodiments of the present invention can function in one of several modes that include a basic mode; a stress reduction/relaxation mode; an anti-snoring; and a fitness training/cardio. The functionality of each of these modes is described in further detail below.

The Basic mode can be used for all applications of breath regulation and training. In this mode, the user can set the output volume, as well as choose an effects preset (such as reverb).

The Anti-Snore mode can detect the wave frequency and volume of a snore. In this mode, the output volume incrementally increases as the input volume increases, to make the breath audible to the sleeping person. The breath becomes audible (without the person fully waking up) and acts as a cue for the user to breathe more quietly. When the input breathing becomes quieter and more like normal breathing, the audio feedback matches the new softer volume with a softer output volume and returns to Basic mode.

The Stress Reduction/Relaxation mode adds other sounds along with the user's breath such as water sounds, nature sounds, music, or a drone. The addition of these sounds enhances relaxed breathing patterns. In this mode, the user can choose the background sound from pre-programmed options.

The Fitness Training or Cardio Mode adds the sound of a pulse along with the user's breath. The pulse acts as a cue for the user to breathe at a certain rate or tempo, supporting cardio programs and heart rate variability training. The user can set rate and volume of the pulse.

Signal processing: In one embodiment, the signal processing can be an analog-based processing, having a real-time micro-controller based sampling and control. The micro-controller can process the incoming microphone signal and compute a desired output level based on various algorithms. In one exemplary processing of the audio signal, the microphone signal is first pre-amplified to a voltage level that can be processed by an audio envelope detector circuit. This circuit includes a peak detector with a time constant slightly longer than the lowest audio input frequency expected, in this case approximately 100 Hz. The envelope detector signal is then fed into the analog-to-digital converter input of the micro-controller allowing it to constantly sample the input volume level. The micro-controller then controls the final output volume level fed to the headphones utilizing a digitally controlled variable-gain amplifier. In one embodiment, the final output signal is not modified in any manner from the original input, except in volume.

In addition to controlling the output volume, the micro-controller can measure, track and display various statistical parameters indicating the user's performance improvement or regression over a period of time. The statistical analysis can monitor peak volume, lowest volume and an average volume. For the peak and lowest volumes, parameters such as the length of time at that volume and the number of episodes above a threshold can be tracked.

In addition, the device also includes a playback feature so that a breathing session can be digitally recorded and played back through the display unit's speaker(s).

In another embodiment, the novel breathing biofeedback device uses a DSP to modify and enhance the audio output. The DSP also communicates with the user interface and controls the display. As set forth above and shown in FIG. 2, the DSP controller is configured to enable audio processing as well as a breath state machine.

The DSP audio processing can modify the audio buffers by gain control, equalization, frequency shifts and effects processing. The audio processor can clip the output volume. Since different frequencies have different perceived volumes, the different frequency bands can be clipped independently.

Figure 3:
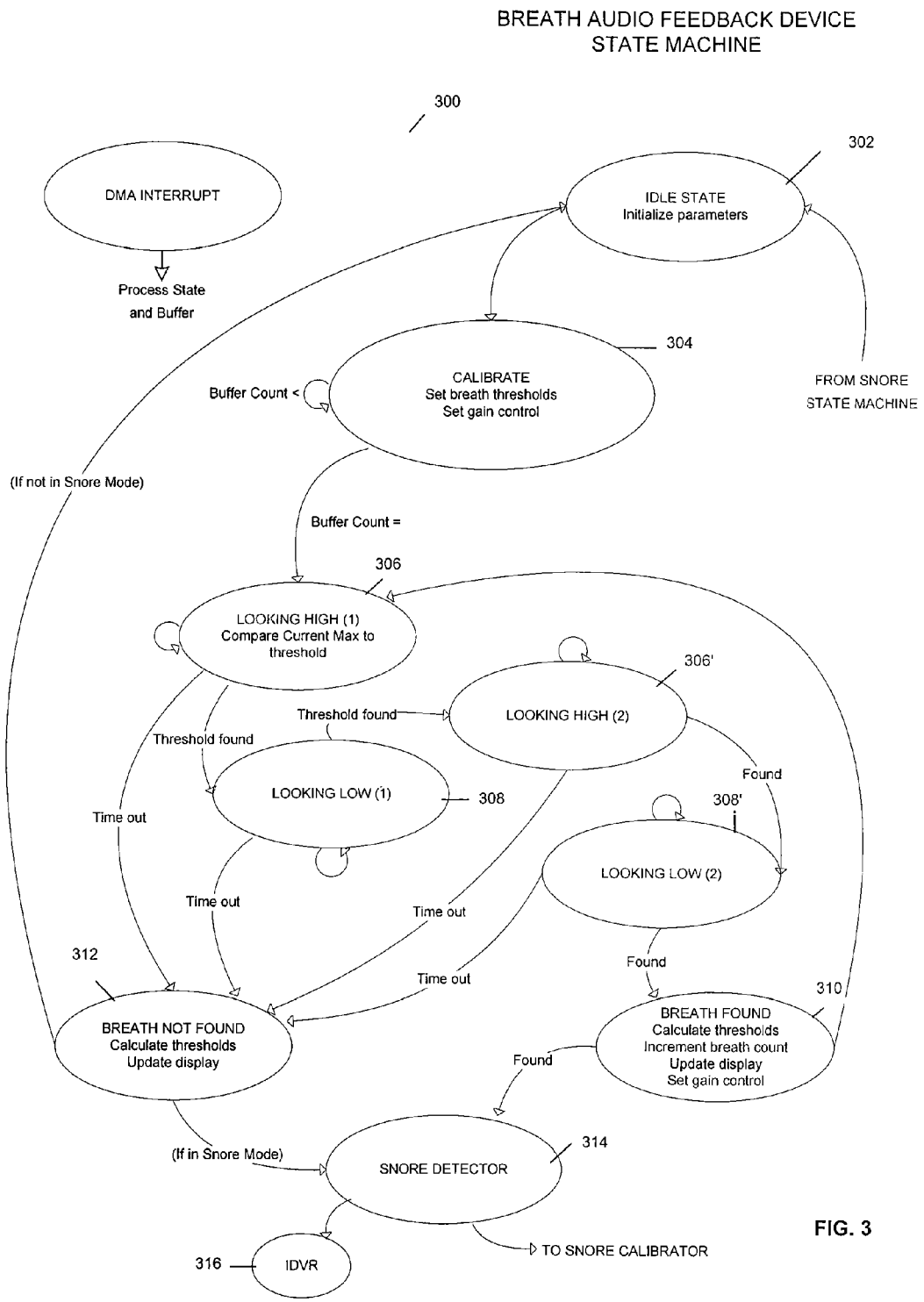
FIG. 3 is an exemplary block diagram of one embodiment of the breath state machine corresponding to the block diagram of FIG. 2.

FIG. 3 shows an exemplary block diagram 300 of one embodiment of the breath state machine. The state machine controls the variables of the audio processor. It first calibrates the device to the incoming breath and then, using the data from the calibration, counts the incoming breaths and modifies the gain and frequency control variables as necessary. The states of the breath state machine are as follows: IDLE 302 ; CALIBRATE 304; PEAK_DETECT (or looking high) 306; TROUGH_DETECT (or looking low) 308; BREATH_FOUND 310 and BREATH_NOT_FOUND 312. Each of these states is described in further detail below.

The IDLE state resets some state parameters. The CALIBRATE state Loops for some time (e.g. 10 seconds) while keeping track of min and max buffer averages. At the end of the calibration time this information is used to calculate the low and high thresholds for the breath detection states. It also resets the gain control variable.

The Breath Detection States can include four breath detection states, that include PEAK_DETECT, TROUGH_DETECT, PEAK_DETECT2, TROUGH_DETECT2. These four states are used to detect the breath itself. This can be done by taking the average of each buffer as it comes in and comparing it to the thresholds established in the 'Calibrate' state. One breath cycle, which includes inhalation and exhalation, has two high peaks and two low troughs. After two peaks and two troughs have been detected the 'BREATH_FOUND' state is entered. If the threshold is not reached within the timeout period the 'BREATH_NOT_FOUND' state is entered.

The BREATH_FOUND state can be configured to recalculate the thresholds, increments the breath counter, update the display, set the gain control, and modify the equalizer parameters (as necessary). After this state the breath detection state returns to PEAK_DETECT for the next breath cycle.

The BREATH_NOT_FOUND state: When no breath is found the device recalibrates itself. The state machine returns to IDLE, where it resets, and the whole process is started again.

A variation of this state machine can be used in an Anti-Snore mode, enabling the device to detect snores and modify the equalizer and gain controls as necessary. The breath state machine can automatically detect a snore and enter snore mode, when the Anti-Snore mode (Snore detector 314) is enabled. When snoring stops, the state machine automatically reverts to the Basic 402 mode or the non Anti-Snore mode. From the snore mode, an integrated digital voice recorder 316 is used to record the breathing sounds.

Figure 4:
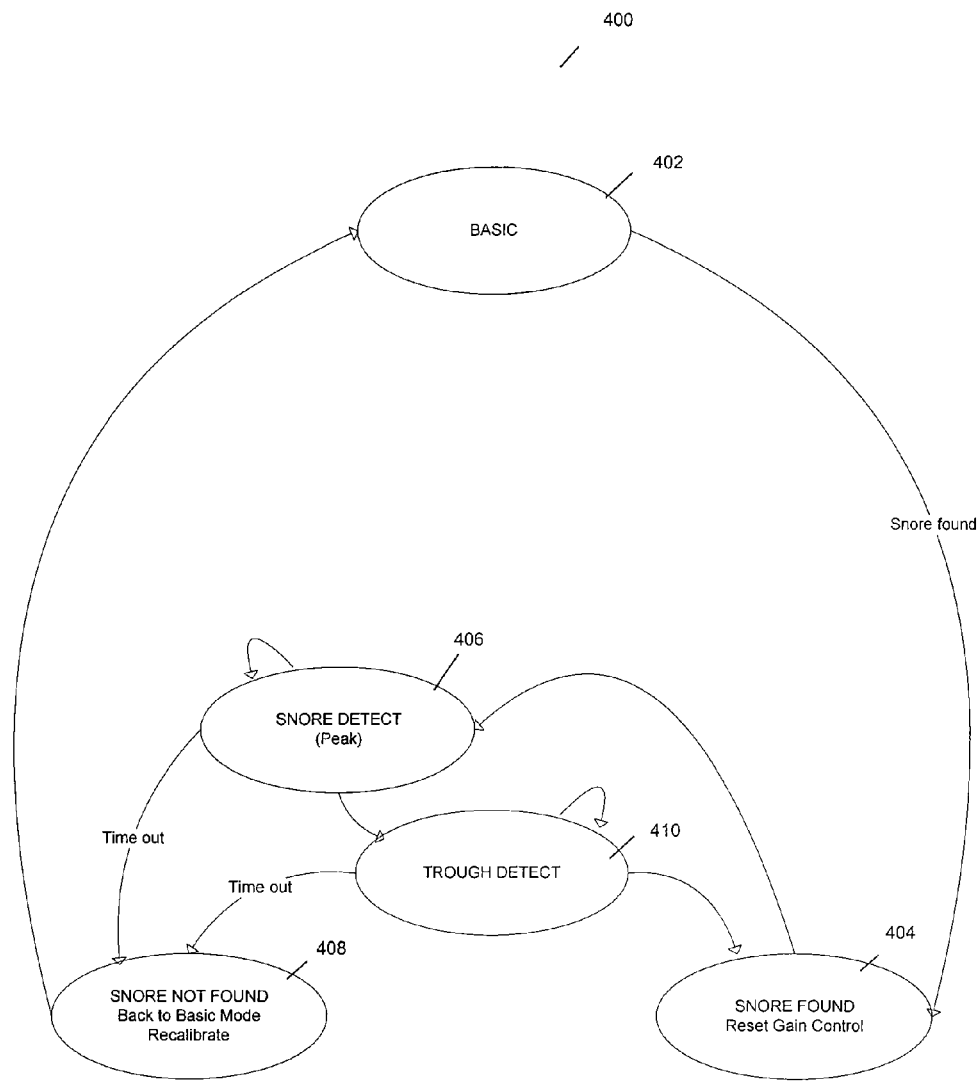
FIG. 4 is an exemplary block diagram of one embodiment of the snore mode of the breath state machine of FIG. 3.

FIG. 4 shows an exemplary block diagram 400 of one embodiment of the snore mode of the breath state machine. As shown in FIG. 4, the snore mode can start in the basic mode 402. Form the basic mode, once a snore is found or sensed 404, the gain control is reset. Control moves to snore detect to detect the peak volume and/or frequency of the snore sound. This continues until a peak is detected. If a peak is not detected, the process times out and the state reverts to the "snore not found" state 408 and then back to the basic mode 402. When a peak for a snore is detected, then a low point volume and/or frequency is searched for 410. When a trough is found, control is passed to the snore found state 404. When a trough is not found after a period of time, the process times out and the state reverts to the "snore not found" state 408 and then back to the basic mode 402. As described above, the Anti-Snore mode can detect the wave frequency and volume of a snore. In this mode, the output volume incrementally increases as the input volume increases, to make the breath audible to the sleeping person. The breath becomes audible (without the person fully waking up) and acts as a cue for the user to breathe more quietly. When the input breathing becomes quieter and more like normal breathing, the audio feedback matches the new softer volume with a softer output volume and returns to Basic mode.

All patents and publications referred to above are incorporated by reference herein.

As will be understood by those skilled in the art, the present invention may be embodied in other specific forms without departing from the essential characteristics thereof. Those skilled in the art will recognize, or be able to ascertain using no more than routine experimentation, many equivalents to the specific embodiments of the invention described herein. Such equivalents are intended to be encompassed by the following claims.

What is claimed is:

1. A breathing biofeedback device, comprising: a microphone configured to convert breathing related sound signals into a first output signal;

a preamplifier amplifying the first output signal to generate a second output signal;

a variable gain amplifier operable to amplify the second output signal in accordance with a gain level signal to generate a third output signal;

a controller comprising an audio envelope detector operable to receive the second output signal from the preamplifier, wherein the controller is operable to generate the gain level signal in response to an analysis of an output of the audio envelope detector and wherein the gain level signal increases in response to an increase in a volume level of the second output signal and decreases in response to a decrease in the volume level of the second output signal;

and earphones operable to convert the third output signal into breathing sound signals output to a user, wherein the controller further comprises a state machine configured to detect a type of breath cycle and further wherein the controller is configured to operate in one of several functional modes based on the type of breath cycle detected, wherein the functional mode is selected from a group consisting of: a basic mode for enabling a user to set one of an output volume and effects preset to the breathing sound signals output to the user, an anti-snore mode operable to detect breath cycles associated with snoring, a stress reduction mode operable to add additional sounds to the breathing sound signals output to the user, and a fitness training mode operable to add a sound of a pulse to the breathing sound signals output to the user.

2. The device of claim 1 further comprising a user interface operatively coupled with the controller.

3. The device of claim 1 wherein in said anti-snore mode the controller is further configured to detect the wave frequency and volume of a snore, and further wherein the gain level increases as the detected volume increases and the gain level decreases as the detected volume decreases.

4. The device of claim 1 wherein in said stress reduction mode the controller is configured to add background sounds operable to enhance relaxed breathing patterns to the breathing sound signals output to the user.

5. The device of claim 1 wherein in said fitness training mode the controller is configured to add the sound of a pulse along with the user's breath, wherein the pulse is operable to provide a cue for the user to breathe at a certain rate.

6. A method for determining breathing biofeedback comprising:

converting breathing related sound signals into a first output signal;

amplifying the first output signal using a preamplifier to generate a second output signal;

generating a third output signal by amplifying the second output signal in accordance with a gain level signal using a variable gain amplifier;

using a digital signal processor (DSP) comprising an audio envelope detector operable to receive the second output signal from the preamplifier to generate the gain level signal in response to an analysis of an output of the audio envelope detector, wherein the gain level signal increases in response to an increase in volume level of the second output signal and decreases in response to a decrease in volume level of the second output signal;

and converting the third output signal to breathing sound signals for output to a user, wherein the digital signal processor further comprises a state machine configured to detect a type of breath cycle and further wherein the digital signal processor is configured to operate in one of several functional modes based on the type of breath cycle detected, wherein the functional mode is selected from a group consisting of: a basic mode for enabling a user to set one of an output volume and effects preset to the breathing sound signals output to the user, an anti-snore mode operable to detect breath cycles associated with snoring, a stress reduction mode operable to add additional sounds to the breathing sound signals output to the user, and a fitness training mode operable to add a sound of a pulse to the breathing sound signals output to the user.

7. The method of claim 6 further comprising using a user interface operatively coupled with the controller to receive input and provide operational information to the user.

8. The device of claim 6 wherein in said anti-snore mode the digital signal processor is further configured to detect the wave frequency and volume of a snore, and further wherein the gain level increases as the detected volume increases and the gain level decreases as the detected volume decreases.

* * * * *